United States Patent
Lehoucq et al.

(10) Patent No.: US 6,533,940 B2
(45) Date of Patent: Mar. 18, 2003

(54) PROCESS FOR SEPARATION IN A SIMULATED MOVING BED OF AT LEAST ONE COMPONENT IN COLUMNS THAT HAVE A SUITABLE LENGTH TO DIAMETER RATIO

(75) Inventors: Sylvie Lehoucq, Vandoeuvre les Nancy (FR); Olivier Ludemann-Hombourger, Chavigny (FR); Roger-Marc Nicoud, Richardmenil (FR); Michel Hamende, Brussels (BE); Emile Cavoy, Ham-sur-Heure (BE)

(73) Assignee: Novasep, Vandoeuvre-les-Nancy Cedex (FR)

( * ) Notice: Subject to any disclaimer, the term of this patent is extended or adjusted under 35 U.S.C. 154(b) by 0 days.

(21) Appl. No.: 09/892,796

(22) Filed: Jun. 28, 2001

(65) Prior Publication Data

US 2002/0011445 A1 Jan. 31, 2002

(30) Foreign Application Priority Data

Jun. 28, 2000 (FR) .............................. 00 08359

(51) Int. Cl.⁷ .............................. B01D 15/08
(52) U.S. Cl. .................... 210/659; 210/198.2
(58) Field of Search ................ 210/635, 656, 210/659, 662, 198.2; 127/46.1, 46.3

(56) References Cited

U.S. PATENT DOCUMENTS

| | | | |
|---|---|---|---|
| 2,985,589 A | 5/1961 | Broughton et al. | 210/659 |
| 4,498,991 A | 2/1985 | Oroskar | 210/659 |
| 4,599,115 A | 7/1986 | Ando et al. | 210/656 |
| 5,114,590 A | 5/1992 | Hotier et al. | 219/659 |
| 5,200,075 A * | 4/1993 | Otani | 210/283 |
| 5,578,215 A | 11/1996 | Hotier et al. | 210/659 |
| 5,578,216 A | 11/1996 | Hotier et al. | 210/659 |
| 6,177,601 B1 * | 1/2001 | Bogdan | 585/419 |

FOREIGN PATENT DOCUMENTS

| | | | | |
|---|---|---|---|---|
| EP | 0 769 316 A1 | 4/1997 | | 210/659 |

OTHER PUBLICATIONS

XP–002167544, Journal of Chromatography A, 666 (1994) 627–650, Elsevier Science B.V., Amsterdam, Preparative chromatographic resolution of racemates on chiral stationaryphases on laboratory and production scales by closed–loop recycling chromatography, Joachim N. Kinkel.

* cited by examiner

Primary Examiner—Ernest G. Therkorn
(74) Attorney, Agent, or Firm—Millen, White, Zelano & Branigan, P.C.

(57) ABSTRACT

The invention relates to a process for separating at least one component of a mixture in a simulated moving bed, in which each of the chromatographic columns that contains an adsorbent has a ratio of L (length) to D (diameter) of between 0.01 and 0.34, and the ratio of $L_{TOT}$ (length in n columns) to D (diameter) is between 0.06 and 2.3. It is possible to apply an axial dynamic pressure on each of the upper columns that exceeds the pressure drop of all of the columns.

11 Claims, No Drawings

PROCESS FOR SEPARATION IN A SIMULATED MOVING BED OF AT LEAST ONE COMPONENT IN COLUMNS THAT HAVE A SUITABLE LENGTH TO DIAMETER RATIO

The invention relates to a process for separation in a simulated moving bed of at least one component of a mixture that contains it.

It applies in particular to the preparative chromatography and especially to the separation of optical isomers, used in the pharmaceutical industry.

The technological background is illustrated by Patents EP-A-0769316 and U.S. Pat, No. 5,114,590.

By discontinuous (batch) chromatography, the tendencies are as follows:

To obtain a good resolution, it is necessary to use a large number of theoretical plates (N). Whereas this number of plates in a chromatographic column increases with the ratio $L/d_p^2$, whereby L is the length of the column and $d_p$ is the mean diameter of the particles that it contains, this means that for a given particle size, the longest columns will be preferable to carry out or to improve a chromatographic separation of a mixture of organic components.

The diameter of a column is calculated by taking into account the pressure drop in the latter. It is common practice to operate with the maximum pressure drop that is acceptable. This means that for a given column length, a smaller column diameter D and thus a large L/D ratio will be preferred.

Practical limitations also conflict with the use of large-diameter columns.

The larger the diameter of the column, the higher the ratio between the diameter of the column and the diameter of the tube that feeds the latter. As shown by Etienne et al., 2$^è$meCongrès de Génie des Procédés [Second Conference of Process Engineering], Toulouse, France, 417–422, 1989, this leads to a non-piston flow distribution at the intake of the column. By increasing the length of the column, the importance of this phenomenon is discounted.

Some authors (C. Dewaele, M. De Coninck, M. Verzele, Separation Science and Technology, 22 (8–10), 1919–1931, 1987) described a loss of effectiveness by using large column diameters, larger than 44 mm, which is reflected by a broadening of chromatographic peaks, and even a splitting of the peaks into two.

The literature describes the L/D ratios between 2 and 11.5 in the range of chiral separations (J. Dingenen and J. N. Kinkel, J. Chromatogr. A, 666, 627–650, 1994).

The limitations that are described in discontinuous (batch) mode are also encountered in the systems with simulated moving bed adsorption (more columns means more edge effects). For example, in U.S. Pat. No. 4,599,115, it is specified that in a simulated moving bed, the use of large-diameter adsorbent beds leads to non-uniform fluid flows and to high costs of installation and putting into service. The authors therefore proposed a simulated moving bed system characterized by a significant reduction of the operating pressure and energy needs as well as by chromatographic columns that have a high L/D ratio.

BRIEF SUMMARY OF THE INVENTION

This tendency has been emphasized during the last decade. By increasing the L/D ratio, however, the authors maximized the number of plates available in the system at the expense of the productivity expressed in grams of product per kilogram of stationary phase and per day. By the same token, pressure constraints led to high costs.

Contrary to what is taught, it has been noted that by using a system of several chromatographic columns in a simulated moving bed for separating organic components from a mixture that has a low ratio of length of each column to diameter, these above-mentioned drawbacks were eliminated.

More specifically, the invention relates to a process for separating at least one component from a mixture that contains it, in a device that comprises a group of chromatographic columns containing an adsorbent (or stationary phase), mounted in series and in a loop, whereby the loop comprises at least one point for an injection of the mixture, at least one point for draw-off of a raffinate, at least one point for an injection of desorbent and at least one point for draw-off of an extract, in which all of the injection points and draw-off points are offset periodically and simultaneously by the same number of columns in a given direction that is defined relative to that of the flow of a main fluid that circulates through the loop, whereby the process is characterized in that the main fluid is circulated in said chromatographic columns, whereby each of them has a length to diameter L/D ratio of between 0.01 and 0.34 and in that the $L_{TOT}/D$ ratio of the total length of the columns to their diameter is between 0.06 and 2.3.

The simulated moving bed system was described in particular in U.S. Pat. No. 2,985,589. It can be operated in simulated counter-current according to this patent or in simulated co-current according to U.S. Pat. No. 4,498,991.

According to a characteristic of the invention, it is advantageous to apply an axial dynamic pressure to each of said columns that is higher than the pressure drop of all of the columns. This dynamic axial compression is generally exerted at the top of the column, by means of, for example, a hydraulic cylinder coupled to a piston, and it prevents the appearance of large dead volumes caused by any movement of the adsorbent phase.

Each column can be kept at a dynamic axial pressure of usually between 3 and 100 bar (1 bar=$10^5$ Pa) and preferably between 25 and 50 bar.

In general, a distribution system that usually comprises a distributor plate, a frit and optionally a grid between the two is inserted in the piston that constitutes the top of the column and in the lower portion or footing of the column. This system is constructed so as to correct the flow distribution defects produced by the changes of sections at the inlet and the outlet of the column.

According to a characteristic of the process, it has been noted that in addition, when the ratio of the total length of the columns ($L_{TOT}$=nL) to the diameter of the column was between 0.06 and 2.3, the daily production of separated product and the productivity of the separation by substantially reducing, moreover, the stationary phase was improved.

It is possible to work with at most 12 columns. It is nevertheless preferred to use a group of 4 to 8 columns.

The main advantage of the invention lies in chiral separations because of the very high price of chiral stationary phases.

It may be advantageous to reduce the dead volumes that are introduced by, for example, the pump for recycling the fluid from the last column into the first, in the chromatographic loop, by adopting the solutions that are recommended in U.S. Pat. No. 5,578,216 of the applicant, namely the suitable reduction of the length of a column that is immediately upstream from the dead volume when the latter is located downstream from said column and upstream from the draw-off flows of said column, or else the suitable reduction of the length of the column that is immediately downstream from said dead volume when this dead volume is located downstream from the injection flows in said column and upstream from said column.

It is also possible to recommend the solution that consists in desynchronizing the alternation periods of the inputs and outputs of fluids according to U.S. Pat. No. 5,578,215.

The invention also relates to a device for implementing the process. It is a device for separation into a simulated moving bed of at least one component of a mixture that contains it, comprising a group of chromatographic columns containing an adsorbent, mounted in series and in a loop, whereby the loop comprises at least one point for an injection of the mixture, at least one point for draw-off of a raffinate, at least one point for an injection of desorbent and at least one point for draw-off of an extract, whereby the device comprises means for offsetting periodically and simultaneously the set of injection points and draw-off points, of the same number of columns in a given direction that is defined relative to that of the flow of the main fluid that circulates through the loop, and means for circulation of the main fluid that are connected to the first column and the last column, whereby the device is characterized in that each of the columns has a ratio of length L to diameter D of between 0.01 and 0.34 and preferably between 0.1 and 0.3 and in that the $L_{TOT}/D$ ratio is between 0.06 and 2.3, preferably between 1 and 2, whereby $L_{TOT}$ is the total length of n columns, and D is the diameter.

According to a characteristic of the invention, the device can comprise means for applying an approximately constant pressure to the piston of the column.

Particles whose grain size is on average less than 100 micrometers are advantageously used.

To carry out a piston-type flow, with large-diameter columns, it is possible to use a suitable fluid distribution system such as the one that is described by Etienne et al., 2èmeCongrès de Génie des Procèdès, Toulouse, France, 417–422, 1989. It makes it possible to ensure good distribution of fluids in axial and radial directions. The lower portion of each column can consist of a stationary part or a moving part (piston, for example) that comprises a distribution system that is approximately identical to that of the top of the column.

According to a characteristic of the device, the loop that constitutes all of the columns can comprise a pump for recycling the main fluid, in particular from the last to the first column. To compensate for the dead volume caused by the recycling pump, the length of the column upstream from the pump and therefore connected to the intake of the latter can be shorter than that of other columns according to U.S. Pat. No. 5,578,216.

According to a variant, all of the columns can have the same length, but it is possible to circulate the main fluid in the column upstream from the recycling pump during a period that is longer than the period of valve switching of other columns, according to U.S. Pat. No. 5,578,215.

The invention will be better understood based on the following examples that are given by way of illustration.

The methodology that is used to identify the conditions of the simulated moving bed is discussed below:

The analysis of the elution profiles that are obtained by high-performance liquid chromatography (HPLC) makes it possible to optimize the operating conditions.

The design and the characteristics of a simulated moving bed are calculated starting from the measurement of the following data described in F. Charton and R. M. Nicoud, J. Chromatogr. A, 702, 97–112, 1995:

The adsorption isotherms that provide the composition of the products in the stationary phase ($C_i$) relative to the composition of products in moving phase $C_i$ when a balance is reached, at a given temperature:

The height of theoretical plateaus (H) based on speed (u) of the moving phase that quantifies the axial dispersion and the mass transfer kinetics;

Pressure drop ($\Delta P$) based on the speed of the moving phase.

The adsorption isotherms are determined by injections of increasing amounts of feedstock for a given speed of the moving phase. Pressure drop $\Delta P$ and the height of theoretical plateau (H) based on speed (u) are determined starting from injections of very small amounts of feedstock at various speeds of the moving phase. These injections are ideally produced in one or more columns of the system in a simulated moving bed.

Current practice calls for determining the operating flows of a simulated moving bed by using the solution of the equilibrium theory according to Mazzotti et al.; J. of Chromatogr. A, 769, 3–24, 1997. This theory, however, relies on the hypothesis of an infinite number of theoretical plateaus, which should be reflected by a long-column system leading to high L/D and $L_{TOT}/D$ ratios.

By taking into account the kinetic and hydrodynamic effects, it was found, surprisingly enough, that the reduction of the length of columns led to an increase in productivity, which totally contradicts the results of the equilibrium theory.

EXAMPLE 1 FOR COMPARISON

Separation of 2-(2-pyrrolidone)butyramide

Description of the separation:
Stationary phase: ChiralPak AD (20 micrometers).
Solubility in an alkane-alcohol mixture.
Moving phase: mixture of n-heptane/n-methanol 40/60 v/v.
Temperature 21° C.
Feedstock at 40 g/l.

The purity constraints are 98.5% for the extract and 90% for the raffinate.

A simulated countercurrent moving bed with 6 columns, each of them with length and diameter equal to 450 mm or L/D=1 and $L_{TOT}/D$=6, is considered. The following configuration of 1-2-2-1, or a column between the inlet of the eluant (moving phase) and the outlet of the extract (zone I), 2 columns between the outlet of the extract and the inlet of the feedstock (zone II), 2 columns between the inlet of the feedstock and the outlet of the raffinate (zone III) and a column between the outlet of the raffinate and the inlet of the eluant (zone IV), is adopted.

The optimum operating flow rates for the system are as follows:

$Q_1$=271.63 l/h.
$Q_{Extract}$=88.83 l/h.
$Q_{Feedstock}$=26.17 l/h.
$Q_{Raffinate}$=24.05 l/h.

The alternation period of the valves is 23.3 minutes (travel of the zones in the direction of the flow of the fluids of a column).

Dynamic pressure applied on each bed: 40 bar (1 bar=$10^5$ Pa).
Pressure drop $\Delta P$ on the entire system=30 bar.
N=724 theoretical plateaus for a column.

The system contains 240 kg of chiral phase. 25 kg of racemic compound is produced per day at the desired purity and with a productivity of 0.105 kg of racemic compound per kg of stationary phase and per day.

EXAMPLE 2 FOR COMPARISON

Example 1 is repeated, but with a simulated countercurrent moving bed system with 6 columns that exhibits the configuration 1-2-2-1 with individual length L=320 mm and diameter D=800 mm, or L/D=0.4.

The operating flow rates are selected to lead to the same pressure drop $\Delta P$ over the entire system as that in Example 1 ($\Delta P$=30 bar). They have the following values:

$Q_1$=1223.3 l/h.
$Q_{Extract}$=343.4 l/h.
$Q_{Feedstock}$=183.1 l/h.
$Q_{Raffinate}$=154.8 l/h.

The switching time of valves $\Delta T$ is 1.75 minutes, N=360 theoretical plateaus per column.

The system contains 543 kg of the chiral phase.

The daily production is 175.8 kg of racemic compound at the desired purity and the productivity of 0.32 kg of racemic compound per kilogram of the stationary phase per day.

EXAMPLE 3 ACCORDING TO THE INVENTION

Example 1 is repeated, but the simulated countercurrent moving bed comprises 14 columns in the configuration 2-5-5-2, with individual length L=96 mm and diameter D=800 mm or L/D=0.12 and $L_{TOT}$/D=1.68.

To lead to same pressure drop $\Delta P$ over the entire system than that of Example 1, the following flow rates are adopted:

$Q_{Recycling}$=1747.4 l/h.
$Q_{Extract}$=520.7 l/h.
$Q_{Feedstock}$=295.6 l/h.
$Q_{Raffinate}$=216 l/h.
Period ($\Delta T$)=2.23 minutes.
N=76 theoretical plateaus/column.

The system contains 380 kg of chiral phase.

The daily production is 283.7 kg of racemic compound and the productivity is 0.747 kg of racemic compound per phase kilogram and per day.

EXAMPLE 4 ACCORDING TO THE INVENTION

The system of Example 1 is repeated, but with 6 columns, each of which has a length of 96 mm and a diameter of 800 mm, or an L/D ratio of 0.12 and an $L_{TOTAL}$/D ratio of 0.72.

The optimum flow rates are selected to lead to the same pressure drop over the entire system as that of Example 1 ($\Delta P$=30 bar).

$Q_{Recycling}$=4583 l/h.
$Q_{Extract}$=1517 l/h.
$Q_{Feedstock}$=300 l/h.
$Q_{Raffinate}$=980 l/h.
Period ($\Delta T$)=1.06 minutes.

These operating conditions lead to the desired purity (98.5% for the extract and 90% for the raffinate) even if the effectiveness of the column is limited to 33 theoretical plateaus per column.

The system contains 163 kg of chiral phase.

The daily production in this case is 288 kg of racemic compound, and the productivity is 1.76 kg of racemic compound per kg of stationary phase and per day.

EXAMPLE 5 FOR COMPARISON

2-[4-(4-Chlorobenzhydryl)piperazin-1-yl]-ethoxyacetamide

Chiral phase: ChiralPak AD (20 micrometers).
Desorbent: 50/50 Mixture of n-heptane and n-propanol.
Temperature: 40° C.
Feedstock at 40 g/l of solution.
Purity constraints 99% for the extract and 85% for the raffinate.
Number of columns=10. Configuration 2-4-3-1.
Individual length L=68 mm.
Diameter: 202 mm.
L/D=0.336 and $L_{TOT}$/D=3.36.
Pressure drop $\Delta P$ over the entire system=30 bar.
Operating flow rates for the required purity:
$Q_1$: 280.3 l/h
$Q_{Extract}$: 82/h
$Q_{Feedstock}$: 11.9 l/h
$Q_{Raffinate}$: 33.3 l/h
Period $\Delta T$=0.93 minute.

The system contains 13 kg of chiral phase.

The daily production is 11.4 kg of racemic compound, and the productivity is 0.88 kg of racemic compound per kilogram of stationary phase and per day.

EXAMPLE 6 ACCORDING TO THE INVENTION

Example 5 is repeated, but with the following different parameters:
Number of columns=6. Configuration 1-2-2-1.
Individual length L=68 mm.
Diameter=202 mm.
L/D=0.336 and $L_{TOT}$=2.02.
Pressure drop $\Delta P$ over the entire system=30 bar.
Operating flow rates for the required purity:
$Q_1$: 393 l/h.
$Q_{Extract}$: 13 l/h.
$Q_{Feedstock}$: 11 l/h.
$Q_{Raffinate}$: 64 l/h.
Period $\Delta T$=0.75 minute.
Number of plateaus per column: 18.
Amount of chiral phase: 8 kg.

The daily production is 10.5 kg of racemic compound per day, and the productivity is 1.3 kg of racemic compound per kg of stationary phase and per day.

EXAMPLE 7 FOR COMPARISON

Separation of 3,7,11,15-tetramethyl-2-hexadecen-1-ol (phytol).
Stationary phase Lichoprep SI 60 (24–40 micrometers).
Desorbent: Mixture of n-heptane and ethyl acetate 75–25 v/v.
Temperature 27° C.
Feedstock at 105 g/l of solution of the cis and trans-phytol mixture (33%/66%).
The purity constraints are 99% for the extract and 95% for the raffinate.

Number of columns=8. Configuration 2-2-2-2.
Individual length L=177.5 mm. Diameter 202 mm.
L/D=0.88 and $L_{TOT}/D=7$.

Operating flow rates for the required purity:

$Q_1$: 226 l/h.

$Q_{Extract}$: 32.4/h.

$Q_{Feedstock}$: 7.8 l/h.

$Q_{Raffinate}$: 11.4 l/h.

Period ΔT=2.05 minutes.
Pressure drop ΔP over the entire system=30 bar.
N=400 theoretical plateaus per column.

The system contains 24 kg of chiral phase.

The daily production is 19 kg of racemic compound, and the productivity is 0.8 kg of racemic compound per kilogram of stationary phase and per day.

EXAMPLE 8 ACCORDING TO THE INVENTION

Example 7 is repeated with the same number of columns with the same configuration for the same separation, but with the following different parameters:

Column length: 58 mm.

Diameter: 202 mm.

L/D=0.29 and $L_{TOT}/D=2.29$.

ΔP over the entire system=30 bar.

The operating flow rates for the required purity are:

$Q_r$: 565 l/h $Q_{Extract}$: 81 l/h $Q_{Feedstock}$: 19.5 l/h $Q_{Raffinate}$: 29.5 l/h Period (ΔT)=0.27 minute.

The system contains 8 kg of chiral phase.

The daily production is 49 kg of racemic compound, and the productivity is 6 kg of racemic compound per kilogram of stationary phase and per day.

What is claimed is:

1. A process for separation of at least one component from a mixture in a device that comprises a group of chromatographic columns that contain an adsorbent, mounted in series and in a loop, wherein the loop comprises at least one point for an injection of the mixture, at least one point for draw-off of a raffinate, at least one point for an injection of desorbent and at least one point for draw-off of an extract, in which all of the injection points and draw-off points are offset periodically and simultaneously by the same number of columns in a given direction that is defined relative to that of the flow of a main fluid that circulates through the loop, wherein each column has a length to diameter L/D ratio of between 0.01 and 0.34, and the $L_{TOT}/D$ ratio of the total length of the columns to their diameter is between 0.06 and 2.3, said process comprising circulating the main fluid in said group of chromatographic columns.

2. A process according to claim 1, wherein an axial dynamic pressure is applied to the top of each column that exceeds the pressure drop of all of the columns.

3. A process according to claim 2, wherein the pressure is kept constant and equal to a value of between 3 and 100 bar.

4. A process according to claim 3, wherein the pressure is between 25 and 50 bar.

5. A process according to claim 1, wherein the number of columns is less than or equal to 12.

6. A process according to claim 5, wherein the number of columns is between 4 and 8.

7. A process according to claim 1, wherein the adsorbent comprises particles with a grain size of less than 100 micrometers.

8. A process according to claim 1, wherein the L/D ratio is between 0.1 and 0.3, and the $L_{TOT}/D$ ratio is between 1 and 2.

9. A process according to claim 1, wherein the mixture comprises optical isomers.

10. A process according to claim 1, wherein the loop comprises a pump for recycling the main fluid and wherein a dead volume of the recycling pump is compensated for by reducing the length of the column upstream from said pump.

11. A process according to claim 1, wherein the loop comprises a pump for recycling the main fluid, and all of the columns have the same length, and in which each time that an injection point or a draw-off point is located on the column upstream from the recycling pump, there remains a period greater than said period.

* * * * *